(12) United States Patent
Gerding et al.

(10) Patent No.: US 9,683,882 B2
(45) Date of Patent: Jun. 20, 2017

(54) MICROWAVE MODULE

(71) Applicant: KROHNE Messtechnik GmbH, Duisburg (DE)

(72) Inventors: Michael Gerding, Bochum (DE); Michael Deilmann, Essen (DE); Nils Pohl, Meckenheim (DE); Michael Vogt, Bochum (DE); Christian Schulz, Bochum (DE); Timo Jaeschke, Hattingen (DE); Christoph Schmits, Dortmund (DE)

(73) Assignee: KROHNE Messtechnik GmbH, Duisburg (DE)

( * ) Notice: Subject to any disclaimer, the term of this patent is extended or adjusted under 35 U.S.C. 154(b) by 0 days.

(21) Appl. No.: 14/753,532

(22) Filed: Jun. 29, 2015

(65) Prior Publication Data

US 2015/0377682 A1    Dec. 31, 2015

(30) Foreign Application Priority Data

Jun. 30, 2014    (DE) .................. 10 2014 109 120

(51) Int. Cl.
| | |
|---|---|
| G01R 27/04 | (2006.01) |
| G01R 27/32 | (2006.01) |
| G01F 23/00 | (2006.01) |
| G01F 23/28 | (2006.01) |
| G01F 23/284 | (2006.01) |
| G01S 7/03 | (2006.01) |
| G01N 22/00 | (2006.01) |

(52) U.S. Cl.
CPC .......... *G01F 23/284* (2013.01); *G01F 23/00* (2013.01); *G01N 22/00* (2013.01); *G01S 7/032* (2013.01)

(58) Field of Classification Search
CPC ....... G01F 23/284; G01F 23/00; G01N 22/00; G01S 7/032
USPC .................... 324/642, 644; 73/290 R, 290 V
See application file for complete search history.

(56) References Cited

U.S. PATENT DOCUMENTS

| | | | |
|---|---|---|---|
| 7,336,141 | B2 | 2/2008 | Mueller |
| 7,355,547 | B2 | 4/2008 | Nakazawa et al. |
| 8,184,039 | B2 | 5/2012 | Garrod et al. |
| 8,269,666 | B2 | 9/2012 | Schultheiss et al. |
| 8,981,867 | B2 | 3/2015 | Schulz et al. |
| 2004/0212529 | A1* | 10/2004 | Fehrenbach .......... G01F 23/284 342/124 |

(Continued)

FOREIGN PATENT DOCUMENTS

| | | |
|---|---|---|
| DE | 601 31 649 T2 | 4/2009 |
| EP | 2 219 045 B1 | 3/2012 |

OTHER PUBLICATIONS

Jurgen Hasch et al: "Millimeter Wave Technology for Automotive Radar Sensor in the 77 GHz Frequency Band", IEEE Transactions on Mircrowave Theory and Techniques, IEEE Service Center, vol. 60, No. 3, Mar. 2012, pp. 845-860.

(Continued)

*Primary Examiner* — Amy He
(74) *Attorney, Agent, or Firm* — David S. Safran

(57) ABSTRACT

A microwave module 1 for a fill level measuring device 2 operating with the runtime method, has a chip for generating and/or receiving microwave signals and a carrier element. To provide an advantageous as possible microwave module, the chip is located in a cavity 9 of the carrier element 8.

5 Claims, 3 Drawing Sheets

(56) References Cited

U.S. PATENT DOCUMENTS

2010/0103024 A1* 4/2010 Schultheiss ........... G01F 23/284
342/124

OTHER PUBLICATIONS

Nils Pohl; "Fraunhofer Institut"; Annual Report 2012, English Translation of pp. 15-17.

* cited by examiner

MICROWAVE MODULE

BACKGROUND OF THE INVENTION

Field of the Invention

The invention relates to a microwave module for a fill level measuring device operating with the runtime method, having at least one chip for generating and/or receiving microwave signals and having at least one carrier element.

Description of Related Art

In one possibility for measuring the fill level of a medium in a container, microwave signals are emitted in the direction of the surface and the signals reflected there are received. The distance between the measuring device and the surface of the medium can be determined and, from this, the fill level can be determined using known variables of the measuring system. Thus, the measuring method is called runtime or radar method. Furthermore, microwave signals can be generated and emitted continuously or in pulses.

Corresponding measuring devices usually have an electronics unit that generates or processes the microwave signals, and an antenna element that, for example, emits the microwave signals into space or guides them along a conductor path structure—e.g. a wire or rod. The term time domain reflectometry TDR is used in conjunction with the coupling in and out of the signals from a waveguide—also called probe.

In many implementations, a microwave module having a chip, which is used for generating and evaluating or processing signals, is located in the electronics unit.

Thus, U.S. Pat. No. 8,269,666 B2 describes, for example, a microwave module with a chip located on a HF printed circuit board. A metallization is located under the printed circuit board in one implementation. A housing is provided on the side of the printed circuit board, on which the chip is located. A similar construction is also shown in U.S. Pat. No. 7,355,547 B2.

The use of a copper carrier as a heat sink below the chip is given in conjunction with similar microwave modules, for example, in the dissertation "MCM Integration Technologies for 60-80 GHz Applications" by Janusz Grzyb, ETH Zurich, 2004.

A chip and a carrier element carrying this chip can be gathered, for example, from the dissertation "Methoden and Techniken zur Integration von 122 GHz Antennen in miniaturisierte Radarsensoren" by Stefan Beer, Karlsruhe, 2013. Bond wires are disclosed there for connecting the chip to the upper side of the carrier element.

Waveguides, for example, are recommended for emitting microwave signals.

An arrangement with a chip, which is connected to a waveguide via a ring coupler also rat race coupler, for example, is disclosed in the article "SIGE-SCHALTUNGEN—RADAR DER ZUKUNFT?" by Prof. Dr.-Ing. Nils Pohl, Annual Report 2012, Fraunhofer Institute for High Frequency Physics and Radar Techniques FHR, pages 15-17.

An arrangement with a rod antenna is shown, for example, in European Patent Application EP 2 219 045 B1.

One implementation of an antenna element consisting of an opening in a substrate as well as a cap is shown in German Patent Application DE 102 43 671 B3 and corresponding U.S. Pat. No. 7,336,141 B2.

German Patent Application DE 601 31 643 T2 describes different carrier elements for microwave chips.

German Patent Application DE 10 2011 015 894 A1 and corresponding U.S. Pat. No. 8,981,867 B2 show, for example, the coupling in of signals in the antenna element.

SUMMARY OF THE INVENTION

The object of the invention is, thus, to provide an advantageous as possible microwave module for a fill level measuring device operating with the runtime method.

The microwave module according to the invention, in which the above derived and described object is met, is initially and essentially wherein the chip is located in a cavity of the carrier element. Thus, the chip doesn't sit on the carrier element, rather is inserted in a recess or depression as the cavity.

Thereby, in one implementation, the chip and the cavity are designed in such a manner and are aligned to one another so that at least one upper side of the carrier element surrounding the cavity and an upper side of the chip facing the upper side of the carrier element are flush. Thus, in this implementation, the upper side of the chip is located at the same level as at least the upper side that surrounds the cavity in which the chip is located.

In an additional or alternative implementation, the chip and the cavity are designed in such a manner and are aligned to one another so that at least one bond wire connecting the chip to a conductor path structure located on the upper side of the carrier element has a length that is less than or equal to 300 micrometers. This implementation allows that the connection of the chip for transmission of microwave signals to a conductor path structure on the upper side of the carrier element is such that at least one bond wire as connecting element between chip and conductor path structure has a maximum length of 300 micrometers.

In a further implementation, two bond wires are provided that each create a single connection to the conductor path structure and that also each have a maximum length of 300 micrometers.

The chip is connected to at least one antenna element in one implementation.

In an additional implementation, the antenna element consists, at least, of one waveguide in the carrier element and a cap functionally extending the waveguide. The waveguide has a diameter of 2.6 millimeters in one implementation. The antenna element can, thereby, be functionally or also actually connected to further antenna elements.

In one implementation, the chip is connected to at least one ring coupler. The ring coupler is located, thereby, in one implementation, between the chip and the antenna element. In one implementation, the chip is connected to the ring coupler via two bond wires, each having a length less than or equal to 300 micrometers. In one design, each bond wire has a diameter of 17 micrometers.

The carrier element consists, in one implementation, at least of one copper carrier and a dielectric substrate. The dielectric substrate forms the upper side of the carrier element in one design.

In an additional implementation, it is provided in conjunction with an above-mentioned design of the antenna element that one through-contact reaching at least to the copper carrier is located in the substrate of the carrier element, below at least one side part of the cap. Thereby, a through-contact is an essentially vertical electric connection between individual layers of the carrier element. In one implementation, a—correspondingly extended—through-contact or several through-contacts is/are provided in the entire area below the supporting surface of the side part of the cap on the carrier element.

In one implementation, the waveguide is located only in the copper carrier of the carrier element and thus, does not extend into the area of the dielectric substrate.

Further, in one implementation, the cap lies on the upper side of the carrier element, opposite the waveguide. The cap thus further guides the waveguide and closes it on one side. In one design, the cap and the copper carrier are electrically connected to one another.

It is provided in one implementation that the frequency of the microwave signals generated and/or received by the chip is greater than 57 GHz an, in particular is between 57 GHz and 64 GHz or between 75 GHz and 85 GHz.

The invention further relates to a fill level measuring device operating with the runtime method, which has a microwave module according to at least one of the above-described implementations.

In detail, there is a plurality of possibilities for designing and further developing the microwave module according to the invention. Reference is made, on the one hand, to the patent claims subordinate to patent claim 1 and, on the other hand, to the following description of embodiments in conjunction with the drawing. The drawing shows

DETAILED DESCRIPTION OF THE INVENTION

Figure 1:
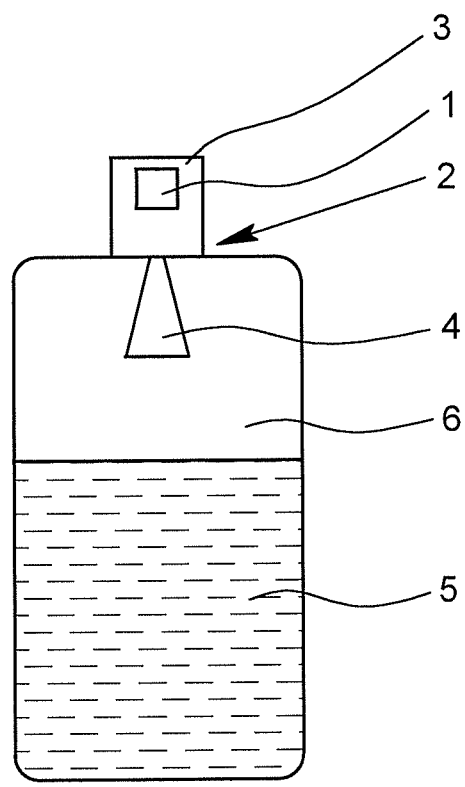
FIG. 1 is a schematic representation of a fill level measuring device.

The use of a microwave module 1 as part of a fill level measuring device 2 is shown schematically in FIG. 1. The microwave module 1 belongs to the electronics unit 3. A horn antenna 4 is provided for emitting and receiving microwave signals with a frequency in the range of 80 GHz.

The fill level of the medium 5 in the container 6 can be determined using the runtime of the microwave signals emitted and received again after being reflected on the surface of the medium 5. Measurement, thus, occurs according to the runtime or radar method.

Figure 2:
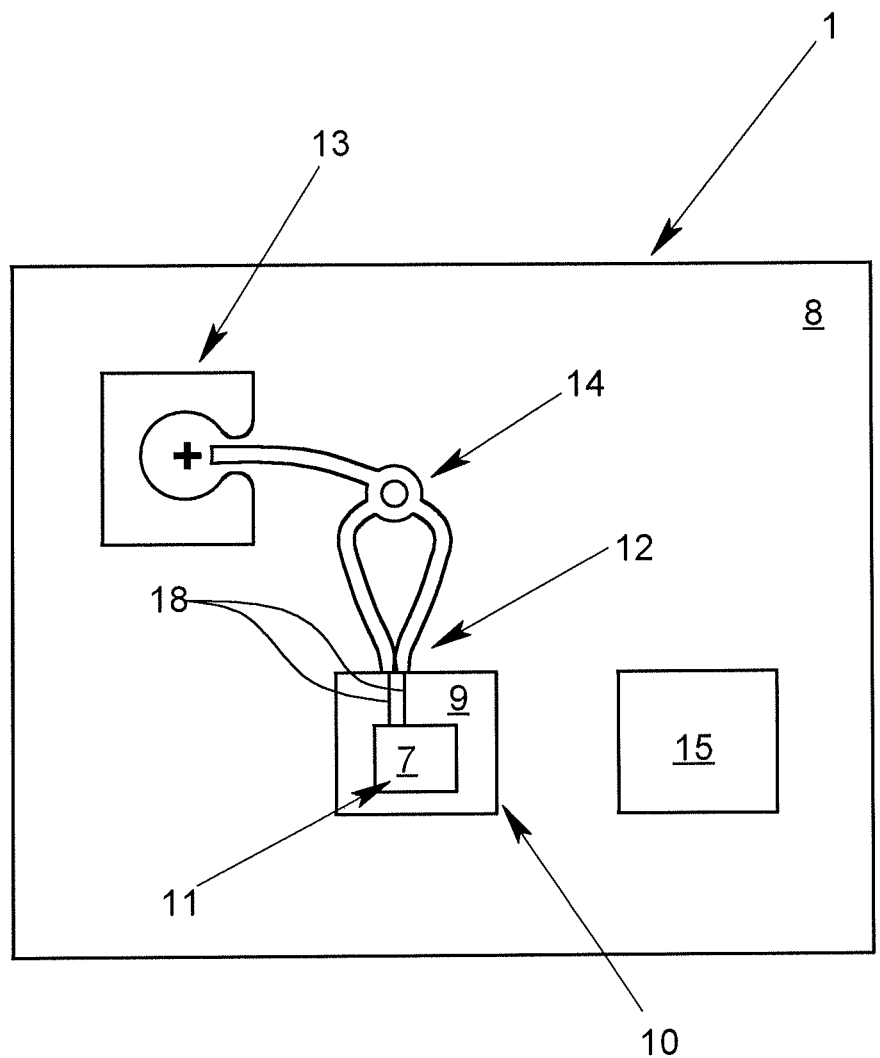
FIG. 2 is a top view of a schematically represented microwave module.

FIG. 2 shows a top view of the microwave module 1, wherein, for clarity, a limitation was made on the components shown.

The main emphasis is in the attachment and the coupling in of the chip that generates or receives and evaluates or processes the microwave signals so that they are available for further evaluation by—not shown here—further components. An alternative name for the chip could be an MMIC monolithic microwave integrated circuit or an ASIC application specific integrated circuit.

The carrier element 8, in which a cavity 9 is located here, is provided for the chip 7. The chip is inserted in the cavity 9 as hollow space or depression. The depth of the cavity 9 is chosen, thereby, depending on the dimensions of the chip 7, so that the upper side 10 of the carrier element 8 and the upper side 11 of the chip are flush with one another. This means that the chip neither extends beyond the upper side 10 of the carrier element 8 nor is it set back or does it lie lower.

The flush arrangement, in particular, has the purpose of implementing the connection from the chip and the conductor path structure 12 on the carrier element 8 to the antenna element to be as short as possible. The direct coupling of the chip—for transmission of microwaves—in the conductor path structure 12 occurs, here, via two bond wires 18.

The two, critical bond wires 18 couple the 80 GHz microwave signals from the chip to the conductor path structure 12, which is located on the upper side 10 of the carrier element. At a frequency in the range of 80 GHz, in particular, parasitic effects that result from a bond wire should be avoided, which result in that a bond wire acts as inductance at such a frequency and, at the same time, capacitively over-couples to a—in particular parallel or adjacently arranged—bond wire. This leads to a loss in power. Thus, in particular, power matching that does not depend on the length of the bond wires should be taken into consideration. Thus, shortening the length of the bond wires 18 is important, which is made possible here by reducing the distance between the chip and the conductor path structure 12 on the upper side 10 of the carrier element 8.

A ring coupler 14 is provided between the antenna element 13 and the chip 7. The ring coupler 14—also called rat race coupler or 180° hybrid—is a directional coupler, which is characterized by its specifications as well as its simplicity.

Overall, the microwave signals are given by the chip differentially over the two bond wires 18 to the conductor path structure 12 and transformed into single ended signals by the ring coupler 14 and, then, are accordingly coupled via a conductor path in the antenna element 13.

Further, purely as an example, a SMD component 15 is indicated here. The function of the microwave module 1, e.g., power supply, controlling the module 1, etc., is ensured by this and further—not shown here—components.

Figure 3:
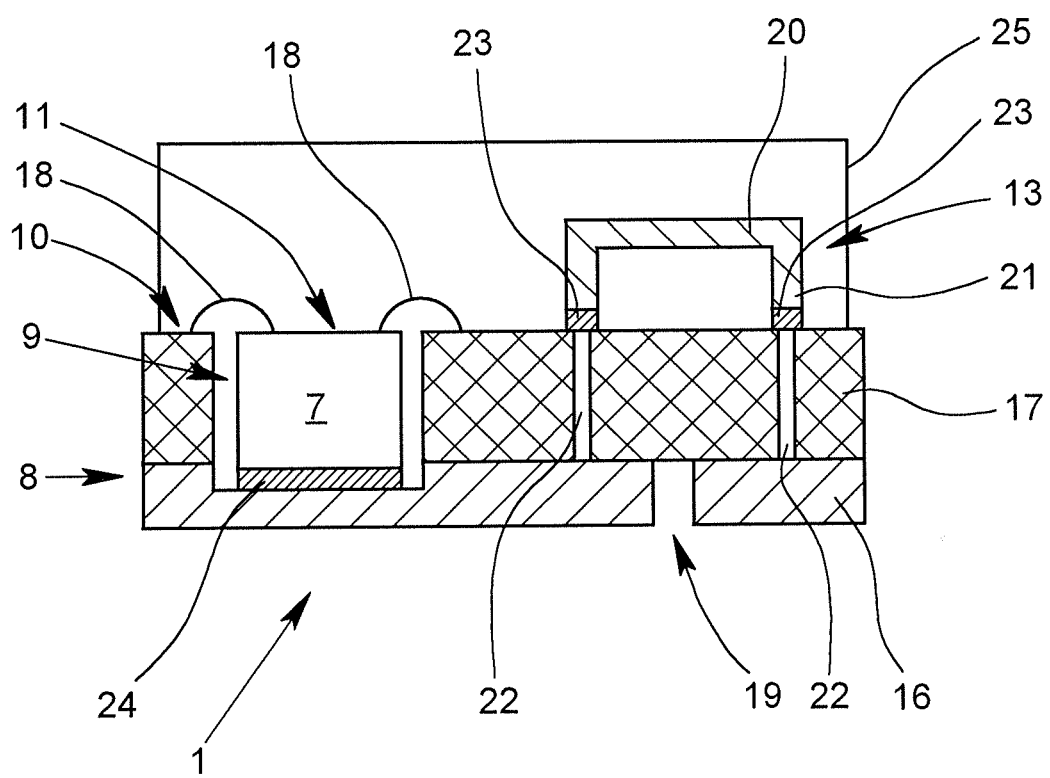
FIG. 3 is a cross section through a further microwave module.

A cross section through a slightly changed variation of a microwave module 1 is shown in FIG. 3. The basic construction, however, conforms to that of the microwave module 1 shown in FIG. 2.

The carrier element is composed of a copper carrier 16 here, this is a 1 mm thick copper layer and of a dielectric substrate 17, which, for example, is made of a glass fiber reinforced plastic laminate. The substrate 17 thereby forms the upper side 10 of the carrier element.

It can be seen that the cavity 9 is designed so that the upper side 11 of the chip and the upper side 10 of the carrier element end flush. This allows for the bond wires 18 to be designed short enough for connecting the chip to the conductor path structure on the upper side 10 of the carrier element, here, in particular, with a maximum length of 300 micrometers. In the shown example, the chip has a height of 190 micrometers and the substrate 17 a thickness of 127 micrometers.

It can be further seen that the antenna element 13 is constructed of a waveguide 19 as recess in the copper carrier 16, and a cap 20 on the upper side 10 of the carrier element. The cap 20, thereby, forms the functional extension of the waveguide 19 and is arranged so that the waveguide 19 is located centrally underneath it. The waveguide 19, here, has a diameter of 2.6 millimeters.

Thereby, the coupling in and out of the microwave signals occurs—as can be seen in FIG. 2—using the conductor path, which leads to the area of the waveguide 19.

The waveguide 19 extends over the area of the copper carrier 16 and ends before the substrate 17. The cap 20 is set with its side parts 21 completely surrounding on the upper side 10 of the carrier element 8 and is electrically connected or in electric contact with the copper carrier 16 through the through-contacts 22.

Overall, the antenna element 13, which, for example, merges into the antenna shown in FIG. 1, arises from the waveguide 19, the through-contacts 22 and the cap 20. Thereby, the cap 20 and the through-contacts 22 are electro-conductively connected to the copper carrier 16, in which the waveguide 19 is located as recess.

In order to attach the, here, closed and cup-shaped cap 20, a conductive adhesive 23 is provided, which also is used for electric contact to the copper carrier 16.

It can be further seen that the chip rests in the cavity 9 on an adhesive pad 24, which is also relevant for the specifications of the depth of the cavity 9.

The elements on the upper side 10 of the carrier element 8 are, finally, protected from mechanical stress by a cover 25. The cover 25 is thereby also used as a high-frequency shield.

What is claimed is:

1. A microwave module for a fill level measuring device operating with the runtime method, comprising:
    at least one chip for at least one of generating and receiving microwave signals, and having at least one carrier element,
    wherein the chip is located in a cavity of the carrier element,
    wherein the chip is connected to at least one antenna element,
    wherein the antenna element comprises a waveguide in the carrier element and a cap functionally extending the waveguide,
    wherein the carrier element comprises at least one copper carrier and one dielectric substrate that form an upper side of the carrier element,
    wherein at least one through-contact is located in the substrate of the carrier element reaching at least to the copper carrier, below at least one side part of the cap and
    wherein the waveguide is only located in the copper carrier of the carrier element and the cap is located opposite the waveguide on the upper side of the carrier element.

2. The microwave module according to claim 1, wherein the chip and the cavity are configured and aligned relative to one another so that at least an upper side of the carrier element surrounds the cavity and is flush with an upper side of the chip that faces the upper side of the carrier element.

3. The microwave module according to claim 1, wherein the chip and the cavity are configured and aligned relative to one another so that at least one bond wire connecting the chip to a conductor path structure located on the upper side the carrier element has a length that is at most 300 micrometers.

4. The microwave module according to claim 1, wherein the chip is connected to at least one ring coupler.

5. The microwave module according to claim 1, wherein the chip is able to at least one of generate and receive microwave signals having a frequency greater than 57 GHz.

* * * * *